(12) United States Patent
Igaki et al.

(10) Patent No.: US 9,668,897 B2
(45) Date of Patent: Jun. 6, 2017

(54) STENT COVER MEMBER AND STENT APPARATUS

(75) Inventors: Keiji Igaki, Kyoto (JP); Hirokazu Yamada, Kyoto (JP)

(73) Assignee: Kyoto Medical Planning Co., Ltd., Tokyo (JP)

( * ) Notice: Subject to any disclaimer, the term of this patent is extended or adjusted under 35 U.S.C. 154(b) by 660 days.

(21) Appl. No.: 13/811,190

(22) PCT Filed: Jul. 19, 2011

(86) PCT No.: PCT/JP2011/004080
§ 371 (c)(1),
(2), (4) Date: Jan. 18, 2013

(87) PCT Pub. No.: WO2012/011269
PCT Pub. Date: Jan. 26, 2012

(65) Prior Publication Data
US 2013/0131778 A1     May 23, 2013

(30) Foreign Application Priority Data

Jul. 20, 2010 (JP) ................................. 2010-163377
Apr. 5, 2011 (JP) ................................. 2011-083374

(51) Int. Cl.
*A61F 2/95*        (2013.01)
*A61L 31/10*     (2006.01)
(Continued)

(52) U.S. Cl.
CPC ................. *A61F 2/95* (2013.01); *A61F 2/86* (2013.01); *A61F 2/89* (2013.01); *A61L 31/10* (2013.01);
(Continued)

(58) Field of Classification Search
CPC ........ A61F 2/82; A61F 2/07; A61F 2002/075; A61F 2250/003; A61F 2210/0004; A61L 2300/416
See application file for complete search history.

(56) References Cited

U.S. PATENT DOCUMENTS 5,980,564 A * 11/1999 Stinson .................. 623/23.7
6,500,204 B1 * 12/2002 Igaki ..................... 623/1.18
(Continued)

FOREIGN PATENT DOCUMENTS

CA       2 563 130       4/2008
JP     2008-253707    * 10/2008
(Continued)

OTHER PUBLICATIONS

European Patent Office, extended European Search Report issued in connection with European Patent Application No. 11809445.7, dated Dec. 6, 2013. (6 pages).

*Primary Examiner* — Anh Dang
(74) *Attorney, Agent, or Firm* — K&L Gates LLP

(57) ABSTRACT

Present invention is a stent apparatus wherein a stent covering member holds a stent, which scaffolds a blood vessel from the inside when implanted in the blood vessel, in contracted state. The stent is formed of a biodegradable polylactic acid (PLA) as a tubular shape, shape memorized to a size capable of, when implanted in a vessel, scaffolding the blood vessel from the inside. This stent is held by the stent covering member in contracted state and mounted on a balloon of a balloon. The covering member is formed of a biodegradable polymer having elasticity as a cylindrical shape having an inner diameter to keep the stent in contracted state and, when the stent is expanded to the shape memorized shape, plastically deformed to release the hold- (Continued)

ing of the stent. The stent and the stent covering member disappear in a vessel after they are implanted in the vessel.

7 Claims, 8 Drawing Sheets

(51) Int. Cl.
- *A61L 31/14* (2006.01)
- *A61F 2/86* (2013.01)
- *A61F 2/89* (2013.01)
- *A61L 31/16* (2006.01)
- *A61F 2/07* (2013.01)

(52) U.S. Cl.
CPC ............... *A61L 31/14* (2013.01); *A61L 31/16* (2013.01); *A61F 2/07* (2013.01); *A61F 2002/075* (2013.01); *A61F 2210/0004* (2013.01); *A61F 2250/003* (2013.01); *A61L 2300/416* (2013.01); *A61L 2400/16* (2013.01)

(56) References Cited

U.S. PATENT DOCUMENTS

| | | | |
|---|---|---|---|
| 2003/0050692 A1* | 3/2003 | Sirhan et al. | 623/1.42 |
| 2003/0060874 A1 | 3/2003 | Igaki | |
| 2003/0153971 A1 | 8/2003 | Chandrasekaran | |
| 2005/0033399 A1 | 2/2005 | Richter | |
| 2006/0200230 A1 | 9/2006 | Richter | |
| 2008/0221670 A1 | 9/2008 | Clerc et al. | |
| 2009/0306677 A1* | 12/2009 | Otto et al. | 606/108 |

FOREIGN PATENT DOCUMENTS

| | | |
|---|---|---|
| WO | 03/060288 | 7/2003 |
| WO | 2004/012630 | 2/2004 |
| WO | 2009/044291 | 4/2009 |

\* cited by examiner

STENT COVER MEMBER AND STENT APPARATUS

CROSS REFERENCE TO RELATED APPLICATIONS

The present application is a National Stage of International Application No. PCT/JP2011/004080 filed Jul. 19, 2011 and which claims priority to Japanese Patent Application No. JP2010-163377 filed Jul. 20, 2010 and No. JP2011-083374 filed Apr. 5, 2011, the entire contents of which are being incorporated herein by reference.

BACKGROUND

Technical Field

This invention relates to a stent covering member for holding a stent, which is to be expanded in diameter when implanted into a vessel such as blood vessels to scaffold the vessel from inside, in contracted state and a stent apparatus using this stent covering member.

Background Art

Heretofore, when stenosis occurs in a blood vessel, such as coronary artery, percutaneous transluminal coronary angioplasty (PTCA) employing stenting is performed in which the stenosed portion is expanded by using a medical balloon catheter, and a cylindrical stent is implanted into this expanded portion for scaffold the vessel from inside so as to ensure the blood flow.

The inventor of the present invention has proposed a stent formed of a biodegradable polymer which, once implanted in a blood vessel of a living body, disappears in the living body after passage of a period of time in WO92/15342(PLT 1), WO00/13737(PLT 2) and WO2009/157164(PLT 3).

These stents are formed of a biodegradable polymer having shape memory property as a cylindrical body and shape memorized to an expanded size to scaffold the blood vessel from inside. These stents are, once implanted in a blood vessel, heated by body temperature to expand to the shape memorized outer diameter and keep the expanded state to scaffold blood vessels from inside. The stent of this kind is mounted on a catheter, inserted together with the catheter into a blood vessel and implanted in a lesion site in the vessel.

The stent expanded to a size to scaffold a blood vessel is contracted to a size having an outer diameter sufficiently smaller than the shape memorized size and mounted on the catheter in this contracted state.

It should be noted that, when the stent formed of the biodegradable polymer material is heated by body temperature and expanded to the shape memorized outer diameter, the diameter is gradually expanded over a sufficient period of time rather than immediately due to the nature of the material. This is because the biodegradable polymer material has a property as a viscoelastic body and viscous resistance is produced when it expands to the shape memorized size. As explained hereinabove, the expansion of the stent needs a certain length of time.

The stent formed by using a biodegradable polymer material is delivered to an implantation position within the blood vessel, that is a lesion site, and then immediately expanded in diameter so that it is expanded to a size to scaffold the inner wall of the blood vessel by utilizing inflation force of a balloon capable of being rapidly expanded with injection of an expansion media.

The stent formed by using a biodegradable polymer material to be expanded by the above described balloon inflation force is mounted, in a contracted state, on the balloon which has been mounted on a tip of a catheter in a folded state, and is transported to the implantation site together with this balloon. When transported to the desired implantation position in the blood vessel, the stent is implanted at the lesion site by supplying the expansion media into the balloon and rapidly expanding the stent to a size to scaffold the blood vessel from the inside. The once expanded stent formed by using a biodegradable polymer material keeps the shape memorized size by its self-expansion force even after the balloon is deflated by removal of the expansion medium, thereby scaffolding the implanted site from the inside to allow fluid path for blood in the blood vessel.

The stent formed by using a biodegradable polymer material having shape memory property and being shape-memorized to the expanded size to scaffold the blood vessel from the inside in an expanded state is heated by body temperature as it is inserted into the blood vessel, generating self-expansion force to recover the shape from the contracted state to expanded state. By the effect of this shape restoring function, the stent having crimped to the balloon in contracted state is expanded in diameter, thus making a gap between the stent and the balloon. For this reason, dislocation or disengagement might occur between the balloon and the stent mounted onto the balloon due to the friction force generated when the stent contacts with an inner wall of the blood vessel as it is inserted into the blood vessel. The stent disengaged from the balloon cannot be rapidly expanded in diameter with the balloon inflation force, making correct implantation to the intended site such as the lesion site impossible. The stent not disengaged from the balloon but just dislocated relative to the balloon may be subjected to the balloon inflation force unequally along its entire length, resulting in its unequal expansion along its entire length. The stent expanded unequally along its length cannot scaffold the vessel wall in the vessel as intended.

It is reported that, in PTCA, when stenting is employed, restenosis occurs in high probability. To prevent this restenosis, drug-eluting stents have been proposed e.g. in Japanese Unexamined Patent Application Publication No. 2008-253707(PLT4), in which a coating agent containing a drug having intimal hyperplasia inhibiting efficacy or antithrombotic efficacy is applied to the surface thereof so that the drug is released for a predetermined period of time. In this case, however, if a stent is disengaged from a balloon or dislocated, thus disabling a correct implantation of the stent at a desired indwelling position, the drug carried by this stent cannot be released at a desired drug administration site.

In order to solve the problem described above, the inventors of the present invention has proposed a stent delivery apparatus wherein a balloon catheter, having a balloon on which the stent is mounted, is inserted into a protective sheath (WO2004/103450:PLT 5). Furthermore, in this stent delivery apparatus, a holding member holds one end of the stent to prevent stent dislocation relative to the balloon, when the stent is extruded from the protective sheath to be expand in diameter.

Citation List

Patent Literature

PLT 1: WO92/15342
PLT 2: WO00/13737
PLT 3: WO2009/157164

PLT 4: Japanese Unexamined Patent Application Publication No. 2008-253707
PLT 5: WO2004/103450

SUMMARY

Technical Problem

Although the above mentioned stent delivery apparatus can prevent expansion of a stent in contracted state to keep a condition in which the stent is mounted on a balloon, using the protective sheath results in a complex structure which is difficult to produce.

Furthermore, in the stent delivery apparatus using the protective sheath, operation for implanting a stent is cumbersome because, after the stent mounted on the balloon is inserted into the vicinity of the implantation site, the protective sheath must be advanced or recessed relative to the catheter so that the balloon protrudes from a tip of the protective sheath.

One of the technical objects of the present invention is to provide a stent covering member in which a stent can be surely mounted and held on a balloon of a balloon catheter without using a protective sheath and the like, wherein the stent is formed of a biodegradable polymer material, shape-memorized to an expanded size larger than an inner diameter of a vessel when inserted into a vessel, expanded by balloon inflation to an expanded state, and heated by body temperature to recover the shape and a stent apparatus using this stent covering member.

Another technical object of the present invention is to provide a stent covering member implanted in a vessel together with a stent formed of a biodegradable polymer material, capable of disappearing in a living body, thereby eliminating the need to take it out from the living body and a stent apparatus using this stent covering member.

Another technical object of the present invention is to provide a stent covering member capable of holding a stent without inhibiting stent expansion conducted by balloon inflation and a stent apparatus using this stent covering member.

Another technical object of the present invention is to provide a stent covering member implanted in a living body together with a stent, thereby releasing a drug to a lesion site in which the stent is implanted to inhibit intimal hyperplasia, and a stent apparatus which can prevent thrombosis.

Solution of Problem

To achieve the above-mentioned technical objects, the present invention provides a stent covering member for covering an outer surface of a stent formed of a biodegradable polymer having a shape memory property as a cylindrical shape and shape memorized to a size capable of scaffolding a vessel from the inside when implanted in the vessel, to hold the stent in contracted state having smaller diameter than the shape memorized size, wherein the stent covering member is formed of a biodegradable polymer having an elasticity as a cylindrical shape having an inner diameter to hold the contracted stent mounted on a balloon of a balloon catheter in contracted state and, when the stent is expanded to the shape memorized size, plastically deformed to release the holding of the stent.

The biodegradable polymer constituting the stent covering member is preferably a copolymer (LCL) of poly-L-lactide (PLLA) and poly-ε-caprolactone (PCL) having a composition ratio of PLLA and PCL within the range of 95 to 20:5 to 80 in molar ratio (mol %).

The stent covering member preferably comprises a plurality of openings formed with 10 to 70% of aperture ratio to the surface area thereof.

The stent covering member may contain at least one of a drug having intimal hyperplasia inhibiting efficacy and a drug having antithrombotic efficacy. An epigallocatechin gallate (EGCg) with a purity of 94% or more may be used for the drug contained in the stent covering member. In this case, 1 to 30 part by weight (wt %) of EGCg is added per 100 part by weight (wt %) of a biodegradable polymer material constituting the stent covering member.

Furthermore, the present invention proposes a stent apparatus comprising a stent formed of a biodegradable polymer material having a shape memory property as a tubular shape and shape memorized to a size capable of scaffolding a vessel from the inside when implanted in the vessel and a stent covering member for covering an outer surface of the stent contracted and mounted on a balloon of a balloon catheter, to hold the stent in contracted state smaller than the shape memorized state.

The stent covering member is formed of a biodegradable polymer having an elasticity as a cylindrical shape having an inner diameter to hold the stent in contracted state and, when the stent is expanded to the shape memorized size, plastically deformed to release the holding of the stent.

The stent covering member preferably has an elastic modulus ranging from $2\times10^7$ to $2\times10^9$ pascal (Pa) at 37 degrees Celsius.

The stent held by the stent covering member is constituted by combining tubular body forming elements formed by bending a continuous strand such that linear parts and bend parts alternate in sequence, and the diameter of the stent is expanded and contracted by altering opening angles of the bend parts.

In the present invention, it is preferable that the stent covering member contains a drug having intimal hyperplasia inhibiting efficacy and the stent contains a drug having antithrombotic efficacy.

A coating agent containing a drug having intimal hyperplasia inhibiting efficacy may be applied to an outer surface of the stent covering member to form a drug containing layer.

Advantageous Effects of Invention

In a stent apparatus using a stent covering member and a stent according to the present invention, since the covering member is formed of a biodegradable polymer having an elasticity as a cylindrical shape having an inner diameter to hold the stent in contracted state, it can surely hold the stent in contracted state, in which self-expansion force works to gradually expand the diameter from the contracted state to the shape memorized state, thereby preventing disengagement or dislocation of the stent from a balloon of a balloon catheter and enabling correct implantation of the stent at an desired implantation site. Moreover, when the stent is expanded to the shape memorized size, the covering member is plastically deformed to release the holding of the stent, so that the covering member does not inhibit stent expansion to the shape memorized expanded size.

In addition, in the stent apparatus according to the present invention, the covering member is also formed of a biodegradable polymer similar to the stent, so that it can disappear together with the stent in a vessel after they are implanted in the vessel, thereby eliminating the need to take them out from a living body such as human body.

Moreover, the stent covering member being formed of a biodegradable copolymer of poly-L-lactide (PLLA) and poly-ε-caprolactone (PCL) having a composition ratio of PLLA and PCL ranging from 95 to 20:5 to 80 in molar ratio (mol %) has improved elasticity in a state of a size to hold a contracted stent and a property in which the elasticity decreases as the diameter is expanded, so that it is plastically deformed. The once expanded stent covering member, therefore, will not elastically recover to a contracted state, so that it does not prevent self-expansion of the stent formed of a biodegradable polymer expanded from the contracted state to the shape memorized size.

In addition, the biodegradable polymer material with a composition ratio of poly-L-lactide (PLLA) and poly-ε-caprolactone (PCL) ranging from 95 to 20:5 to 80 in molar ratio (mol %) has an elasticity and flexibility and is easily deformable according to a curved vessel while restricting deformation in radial direction, thereby enabling insertion into a vessel with an excellent trackability to track the shape of the vessel.

Providing openings with a certain ratio in the stent covering member can prevent the inner wall of the blood vessel from being entirely covered, thereby ensuring blood flow to rami from blood vessel in which the stent is implanted.

Furthermore, since using the stent apparatus according to the present invention enables correct implantation of the stent at a desired implantation site, a drug having intimal hyperplasia inhibiting efficacy may be contained in the stent covering member and implanted together with this stent in a blood vessel, so that this drug is accurately released to an inner wall of a blood vessel of a site in which the stent is implanted, thereby preventing restenosis which might occur due to stent implantation.

In particular, using epigallocatechin gallate (EGCg) with a purity of 94% or more for the drug contained in the stent covering member efficiently inhibits vascular smooth muscle cell proliferation, thereby preventing restenosis for a long period.

In addition, the stent containing a drug having antithrombotic efficacy can release this drug within a blood vessel so as to prevent thrombosis.

Furthermore, both of the stent and the stent covering member may contain drugs, so that larger amount of drug can be contained and, moreover, plural kind of drugs can be simultaneously administered.

Additional features and advantages are described herein, and will be apparent from the following Detailed Description and the figures.

DETAILED DESCRIPTION

Referring to attached drawings, embodiments of a stent covering member according to the present invention and a stent apparatus holding a stent in contracted state on a balloon of a balloon catheter by using this covering member are described hereinafter.

Figure 1:
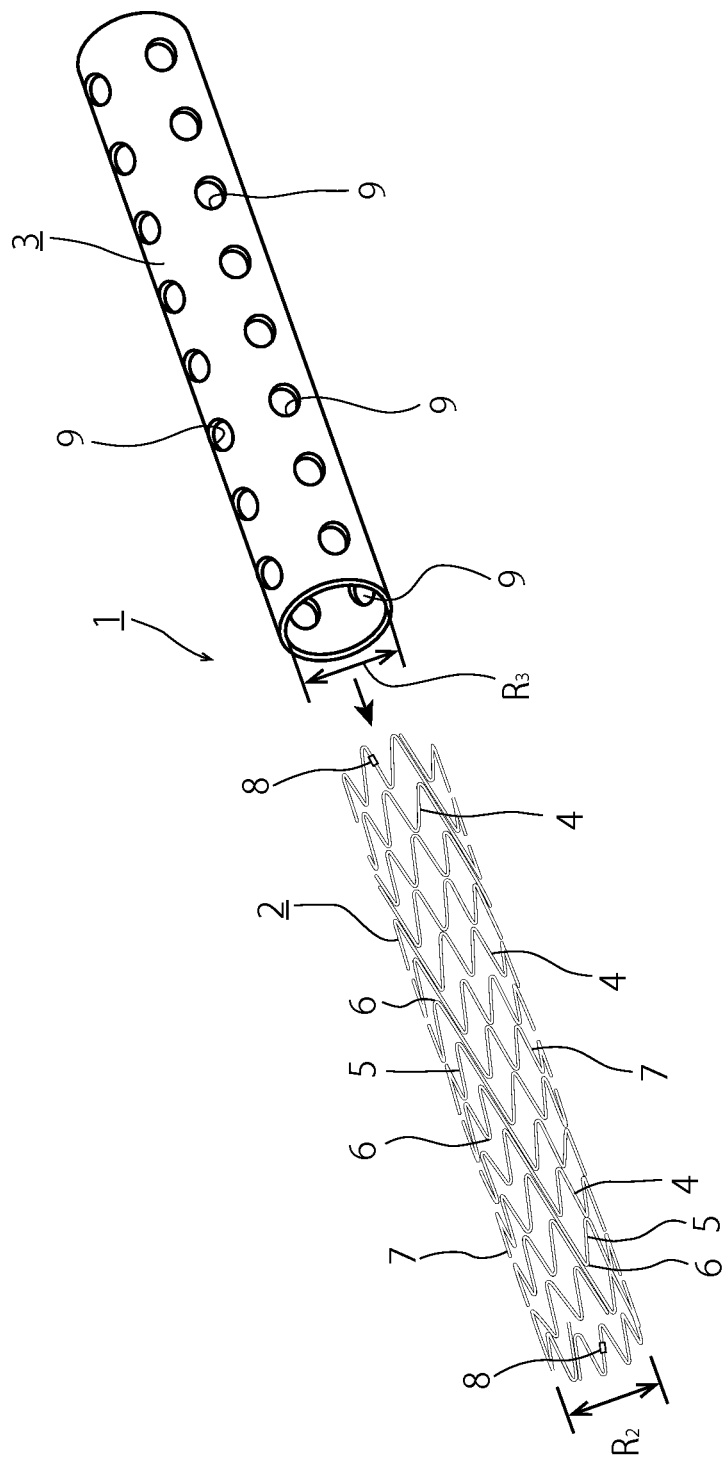
FIG. 1 is a perspective view of a stent covering member according to the present invention and a stent held by this covering member.

As shown in FIG. 1, the stent apparatus 1 using the stent covering member according to the present invention includes a stent 2 formed of a biodegradable polymer material as a tubular shape, shape memorized to a size capable of, when implanted in a vessel of a living body such as an artery, scaffolding the blood vessel from the inside and a stent covering member 3 covering the stent 2 from the outside to hold the stent 2 in contracted state smaller than this shape memorized size.

Figure 2:
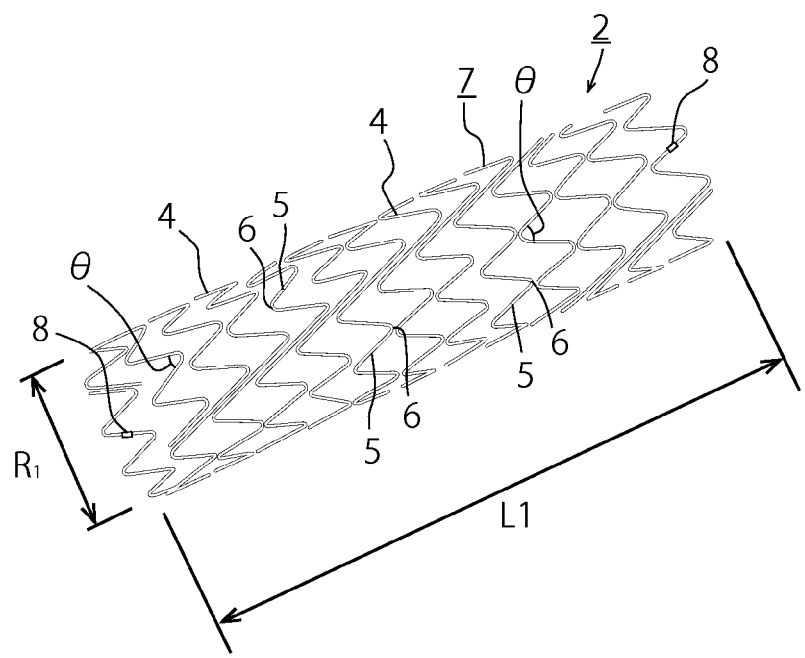
FIG. 2 is a perspective view of a stent expanded to a size for implantation in a blood vessel.

As shown in FIG. 2, the stent 2 used in this embodiment is constituted as a cylindrical body by combining tubular body forming elements 7 formed by bending a continuous strand 4 such that linear parts 5 and bend parts 6 alternate in sequence, to form a single channel from one side to the other side. The dimensions of this stent 2 are appropriately selected in accordance with a living body vessel such as a blood vessel in which the stent 2 is implanted. For example, the stent 2 constituted to be implanted in a blood vessel such as an artery is tubularly shaped wherein the outer diameter R1 is formed to be 2 to 5 mm and the length L1 is formed to be 10 to 40 mm as for the diameters when implanted in the blood vessel. More generally, the stent 2 is formed to have an outer diameter to scaffold the blood vessel in which the stent 2 is implanted from the inside.

Furthermore, the stent 2 is formed of a biodegradable polymer so as not to exert adverse effect on a living body when implanted into a living body such as a human body. As for this biodegradable polymer, a aliphatic polyester having a cross-linked structure realizing the shape memory property, more particularly, any one of polylactic acid (polylactide:PLA), polyglycolic acid (PGA), polyglactin (copolymer of polyglycolic acid and polylactic acid), polydioxanone, polyglyconate (copolymer of trimethylene carbonate and glycolide), and copolymer of polyglycolic acid or polylactic acid and ε-caprolactone can be used. Two or more of these materials can be compounded and used for this biodegradable polymer. Particularly, in view of safety to living bodies, it is desirable to use poly-L-lactide (PLLA) for this biodegradable polymer.

The PLLA used in this embodiment has a glass transition point (Tg) of 55 to 70 degrees Celsius and melting point (Tm) of 170 to 185 degrees Celsius.

In the stent 2 formed by bending the continuous strand 4 in zigzag design such that linear parts 5 and bend parts 6 alternate in sequence and combining the tubular body forming elements 7, increasing the opening angles (θ) of the bend parts 6 of the strand 4 will result in expanded state having a larger diameter and decreasing the opening angles (θ) of the bend parts 6 will result in contracted state having a smaller diameter.

As shown in FIG. 2, the stent 2 formed by bending the continuous strand 4 in zigzag design is shape memorized to the expanded state in which the bend parts 6 of the strand 4 are opened to make the bend angles larger. The size to which the stent 2 is shape memorized is a size enough to scaffold a blood vessel from the inside when implanted in the blood vessel.

The stent 2 shape memorized to the size to scaffold the blood vessel when implanted in the blood vessel is contracted to a size capable of being inserted into the blood vessel, as shown in FIG. 1. This contraction is conducted by applying a pressure to the outer peripheral of the tubularly formed stent 2. For example, this contracted state is achieved compression the stent 2 into contracted state and insert it into a tubular shaped mold having an inner diameter corresponding to the contracted size.

It should be noted that the stent 2 implanted in a living body is invisible by human eye. A stent detecting member 8 capable of being detected by X-ray radiation is therefore attached to the stent 2. This stent detecting member 8 is formed of a metal having a low X-ray transmittance, a stiffness higher than that of the biodegradable polymer and an excellent biocompatibility. In this embodiment, the stent detecting member 8 is formed of gold.

In this embodiment, two stent detecting members 8 are attached to both ends of the stent 2 respectively. The stent detecting members 8 attached to the both ends of the stent 2 facilitate recognition of implantation region of the stent 2 within a blood vessel.

When the stent 2 contracted from the shape memorized size is inserted into a living body and heated by body temperature, self-expansion force works to gradually expand the diameter from the contracted state to the shape memorized state. During transportation within a vessel, if this self-expansion force works to expand the diameter, the expansion of the stent 2 might trigger dislocation against the balloon of the balloon catheter, or disengagement from the balloon due to the friction force generated when the stent 2 contacts with an inner wall of the blood vessel.

In order to prevent these dislocation or disengagement, a stent covering member 3 is used to tightly crimp the stent 2 in contracted state on the balloon of the balloon catheter. This stent covering member 3 is formed of a biodegradable polymer having a certain elasticity as a cylindrical shape. Furthermore, the stent covering member 3 is formed as the cylindrical shape having an inner diameter R3 smaller than the outer diameter R2 of the stent 2 contracted and mounted on a balloon so as to tightly hold the stent 2 in contracted state on the balloon.

It should be noted that the stent covering member 3 desirably holds the stent 2 on the balloon with a certain crimp force so as to prevent dislocation of the contracted stent 2 on the balloon of the balloon catheter. For this reason, stent covering member 3 is formed of a biodegradable polymer having a certain elasticity. Moreover, the stent covering member 3 is preferably formed of the same type of a biodegradable polymer as the stent 2. This is because excellent affinity will assure tighter contact between the stent 2 and the stent covering member 3, so that the stent 2 shape memorized to expanded state can be surely held in contracted state.

In this embodiment, the stent covering member 3 is formed of a copolymer of poly-L-lactide (PLLA) and poly-ε-caprolactone (PCL), which is a kind of aliphatic polyester. The copolymer of the PLLA and PCL used herein has a cross-linked structure and a large elastic force. The elastic force of the copolymer of the PLLA and PCL is larger than that of the poly-L-lactide (PLLA).

Figure 3:
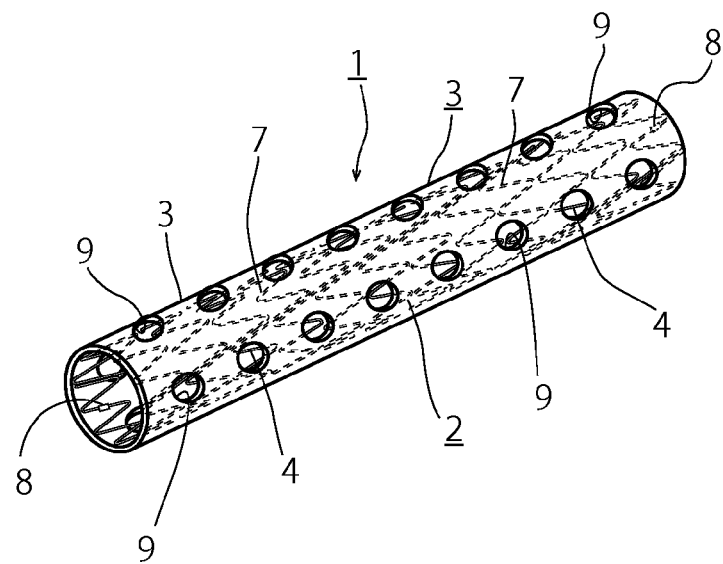
FIG. 3 is a perspective view of a stent apparatus in which a stent covering member holds a contracted stent.
Figure 4:
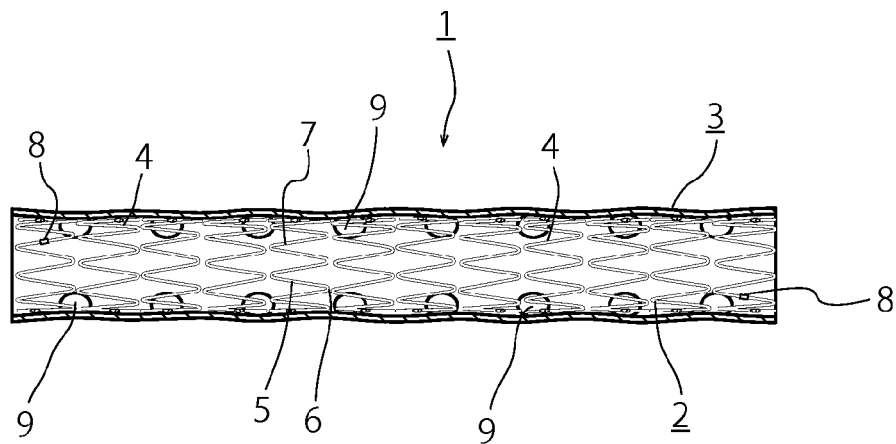
FIG. 4 is a longitudinal sectional view of a stent apparatus according to the present invention.

As shown in FIG. 3, the stent covering member 3 covers the outer peripheral of the stent 2 contracted to a size to be mounted on a balloon and transported within a blood vessel and holds this stent 2 in the contracted state. In this embodiment, the stent covering member 3 is formed of a biodegradable polymer material having an elastic force larger than that of a PLLA-based biodegradable polymer material constituting the stent 2, thereby tightly crimping the outer surface of the stent 2 formed of the PLLA-based biodegradable polymer material and elastically holding this stent 2 in the contracted state.

The stent apparatus 1 according to the present invention, therefore, can keep the stent 2 in contracted state even when it is inserted into a vessel in a living body and heated by body temperature, thereby preventing disengagement or dislocation from the balloon which might triggered by expansion during transportation.

Figure 5:
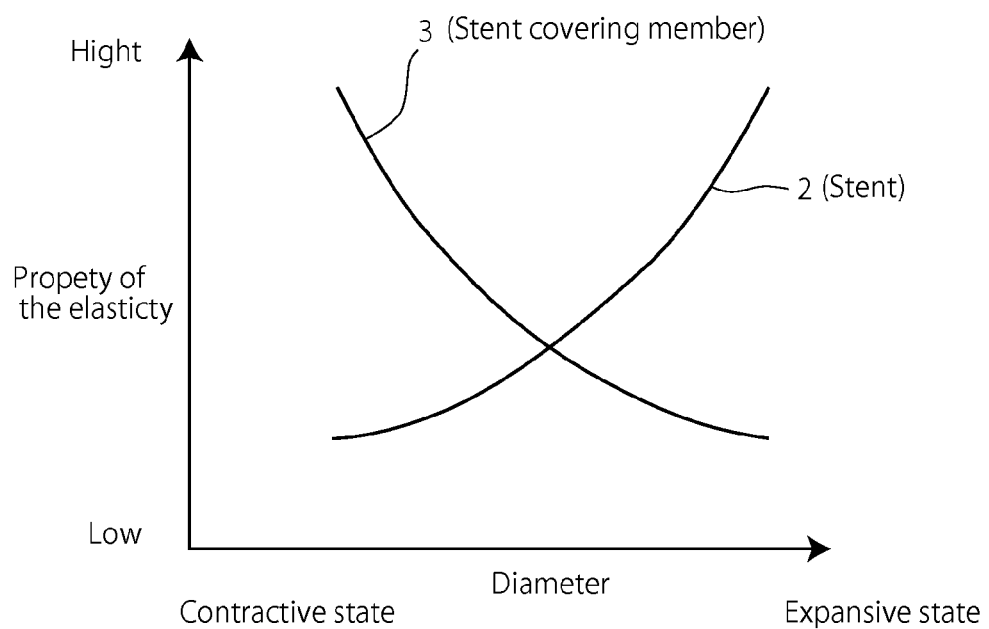
FIG. 5 is a characteristic diagram showing a relationship between elastic property of a stent covering member and expanded state of a stent.

The stent covering member 3 formed of a biodegradable polymer material or a copolymer of PLLA and PCL as a cylinder has a property in which elasticity decreases as it is expanded by balloon inflation from initial state having the contracted inner diameter R3, as shown in FIG. 5. The stent covering member 3 loses the elasticity and is plastically deformed without recovering to the initial size when expansion rate exceeds a certain level. For this reason, if the stent 2 is expanded beyond a certain amount, the stent covering member 3 decreases the elasticity and is plastically deformed. The stent covering member 3 having this property is plastically deformed without elastic recovery when the stent 3 mounted on the balloon of the balloon catheter is expanded beyond a certain amount by the expansion force of the balloon 12. When the stent covering member 3 is expanded to the extent capable of plastic deformation, the stent 2 is expanded to the shape memorized size by the self-recovery force larger than the recovery force of the stent covering member 3 and keeps this state.

In the stent apparatus 1 according to the present invention, since the inner diameter of the stent covering member 3 is formed to a size for holding the outer surface of the stent 2 in contracted state, thereby keeping the stent 2 in contracted state and tightly holding it on a balloon of a balloon catheter, dislocation or disengagement against the balloon can be prevented during insertion into a blood vessel, so that the stent 2 is surely transported to a desired implantation site. Furthermore, the stent covering member 3, capable of being plastically deformed by expanding it by a certain amount, will be plastically deformed when expanded by balloon inflation, thereby allowing the stent 2 shape memorized to an expanded size to expand its diameter without inhibiting the self-recovery force of the stent 2 and realizing the scaffolding of a blood vessel with the stent 2.

Figure 6:
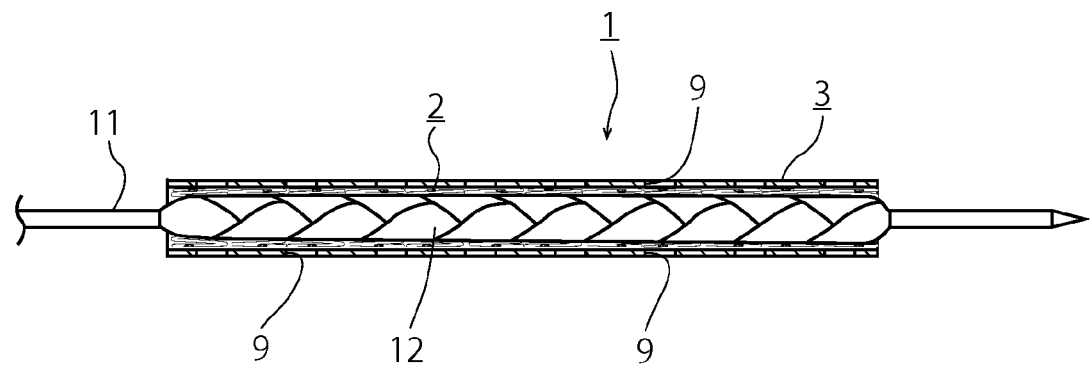
FIG. 6 is a cross sectional view showing a state in which a stent apparatus is mounted on a balloon of a balloon catheter.

In the stent apparatus 1 according to the present invention, as shown in FIG. 6, the stent 2 is held by the stent covering member 3 in contracted state and mounted on the balloon 12 of the balloon 11. The stent apparatus 1 mounted on the balloon 12 is transported together with the balloon catheter through a curved or serpentine blood vessel to a lesion site, which is the implantation site of the stent 2. For this reason, the stent 2 and the stent covering member 3 mounted on the balloon 12 are required to have a trackability to track a bent or curved blood vessel. In addition, the stent covering member 3 is required to have an elasticity to hold the stent 2 in contracted state on the balloon 12. If the stent covering member 3 does not have the required elasticity, it might be folded in the curved and serpentine blood vessel during insertion, the both ends of the stent covering member 3 contacting with inner wall of a blood vessel might injure the blood vessel, or friction and frictional resistance with the inner wall might disable certain holding of the stent 2 on the balloon 12.

In order to solve this problem, in this embodiment, the stent 2 is formed of PLLA, which is easily deformable such that the stent 2 can be inserted into a curved or serpentine blood vessel with excellent trackability. As shown in FIGS. 1 and 2, this stent 2 is constituted as a cylindrical body by combining tubular body forming elements 7 formed by bending a continuous strand 4 such that linear parts 5 and bend parts 6 alternate in sequence, to form a single channel from one side to the other side.

The stent covering member 3 holding this stent 2 in contracted state is formed to have an elastic modulus ranging from $2 \times 10^7$ to $2 \times 10^9$ pascal (Pa) at 37 degrees Celsius, thereby having a flexibility capable of elastic deformation so as not to inhibit deformation of the stent 2 easily deformable in longitudinal direction. When inserted into a blood vessel together with the stent 2, the stent covering member 3 having this elastic modulus can be easily elastically deformed in accordance with the curved and serpentine blood vessel, thereby preventing the stent covering member 3 from injuring a blood vessel by contacting the blood vessel during the insertion. In addition, the stent covering member 3 elastically holding the stent 2 in contracted state can surely hold the stent 2 on the balloon 12, thereby preventing dislocation or disengagement against the balloon 12 during insertion into a blood vessel.

It should be noted that, the stent covering member 3 having an elastic modulus less than $2 \times 10^7$ (PA) can be easily elastically deformed in accordance with a curved blood vessel, but lacks sufficient elasticity to hold the stent 2 in contracted state. On the other hand, the stent covering member 3 having an elastic modulus more than $2 \times 10^9$ (PA) lacks sufficient flexibility, so that it cannot be inserted into a blood vessel with an excellent trackability to track the shape of the blood vessel and, moreover, it has a risk to injure the blood vessel during the insertion.

As stated above, the stent covering member 3 is formed to have an elastic modulus ranging from $2 \times 10^7$ to $2 \times 10^9$ pascal (Pa) at 37 degrees Celsius. Elastic property of the copolymer of PLLA and PCL constituting the stent covering member 3 can be adjusted by appropriately selecting the composition ratio of PLLA and PCL, enabling arbitrary settings of elasticity and flexibility thereof. For example, adding 5 mol % of PCL to PLLA can reduce bending stiffness by half and extremely improve elasticity and flexibility.

On the other hand, in the stent covering member 3 formed of a copolymer of PLLA and PCL, increasing the composition ratio of the PCL will decreases the strength and elastic modulus and increases rupture elongation. The stent covering member 3 formed only of PCL is easily elongated and ruptured by smaller force. On the other hand, if 80 to 90 mol % of PCL is added to PLLA, melting temperature might drop to around human body temperature. If the melting temperature of the stent covering member 3 is around human body temperature or lower, the stent covering member 3 will soften or melt in a blood vessel and consequently it cannot sufficiently hold the stent 2.

For the reasons stated above, the biodegradable polymer material constituting the stent covering member 3 is desirably a copolymer of PLLA and PCL wherein the composition ratio of PLLA and PCL ranges from 95 to 20:5 to 80 in molar ratio (mol %). By setting the composition ratio of PLLA and PCL within the range of 95 to 20:5 to 80 in molar ratio (mol %), the stent covering member 3 having an elastic modulus ranging from $2 \times 10^7$ to $2 \times 10^9$ pascal (Pa) at 37 degrees Celsius can be obtained.

The stent covering member 3 covering the stent 2 is implanted in a state in which the stent covering member 3 contacts an inner wall of a blood vessel. The covering member 3 may contain a drug such that it can effectively administer the drug to an inner wall of a blood vessel in which the stent 2 is implanted. For example, the stent covering member 3 containing a drug having intimal hyperplasia inhibiting efficacy will improve administration effect of the drug and can prevent intimal hyperplasia, incidence rate of which is said to be increased due to stent implantation.

An immunosuppressant or an antitumor agent may be used as the drug having intimal hyperplasia inhibiting efficacy contained in the stent covering member 3. In particular, epigallocatechin gallate (EGCg) having an efficacy having a high antioxidative activity and capable of inhibiting vascular smooth muscle cell proliferation may be used as the drug having intimal hyperplasia inhibiting efficacy. EGCg, a kind of green tea polyphenol, is extracted from green tea. Since EGCg having a higher purity has higher efficacy, an EGCg with a purity of 94% or more is used, and more desirably, an EGCg with a purity of 98% or more is used.

The drug can be contained in the stent covering member 3 by adding the drug to the biodegradable polymer material constituting the covering member 3 and molding this biodegradable polymer material with a molding apparatus.

It should be noted that the drug can be added to the stent covering member 3 without altering physical properties of the stent covering member 3. That is, the drug is added to the material constituting the stent covering member 3 such that elastic modulus thereof can be kept within the range from $2 \times 10^7$ to $2 \times 10^9$ pascal (Pa) at 37 degrees Celsius.

If an EGCg is used for a drug contained in the stent covering member 3, 1 to 30 part by weight (wt %) of EGCg is added per 100 part by weight (wt %) of the biodegradable polymer material. In this embodiment, 1 to 30 part by weight (wt %) of EGCg is added per 100 part by weight (wt %) of a copolymer of PLLA and PCL. The biodegradable polymer material containing EGCg in this range could keep the elastic modulus thereof within the range from $2 \times 10^7$ to $2 \times 10^9$ pascal (Pa) at 37 degrees Celsius.

After the stent apparatus 1 is implanted, the EGCg used for inhibiting vascular smooth muscle cell proliferation is preferably released for six months in controlled release fashion. Adding 1 part by weight (wt %) or more of EGCg per 100 part by weight (wt %) of a copolymer of PLLA and PCL is preferable for the controlled release of EGCg over this period. In order to form the stent covering member 3 having an elastic modulus ranging from $2 \times 10^7$ to $2 \times 10^9$ pascal (Pa) at 37 degrees Celsius, EGCg is preferably 30 part by weight (wt %) or less per 100 part by weight (wt %) of a copolymer of PLLA and PCL.

In view of absolute amount of the drug contained in the stent covering member 3, in order to continue the intimal hyperplasia inhibiting efficacy for six months after the implantation of the stent apparatus 1 into a blood vessel, for the stent covering member 3 used for holding the stent 2 in contracted state having a 2 to 5 mm of outer diameter R1 and a 10 to 40 mm of length L1 as for the dimensions when implanted in the blood vessel, the amount of immunosuppressant or antitumor agent capable of being used for a drug having intimal hyperplasia inhibiting efficacy contained in the stent covering member 3 is preferably 5 to 8 µg per 1 mm of the length.

This amount of the drug desirably contained in the stent covering member 3 can be estimated by the amount of the drug contained in a conventional stent.

In the stent apparatus 1 according to the present invention, it is preferable that stent 2 also contains a drug. The stent 2 containing a drug can administrate the drag directly to a lumen of a blood vessel in which the stent 2 is implanted. The stent 2, therefore, contains a drug having antithrombotic efficacy. One of an anti-platelet agent, an anticoagulant agent and a thrombolytic agent may be used as the drug having antithrombotic efficacy. These drugs can be contained in the stent 2 by adding the drugs to the biodegradable polymer material constituting the stent 2. Alternatively, a biodegradable polymer solution containing a drug may be applied to a surface of the stent 2 to form a drug containing layer.

As stated above, the stent covering member 3 containing a drug having intimal hyperplasia inhibiting efficacy and the stent 2 containing a drug having antithrombotic efficacy make it possible for the drug having intimal hyperplasia inhibiting efficacy to be efficiently administered to an inner wall of a blood vessel in which the stent apparatus 1 is implanted and for the drug having antithrombotic efficacy to be administered to a lumen of the blood vessel, thereby improving intimal hyperplasia inhibiting efficacy and antithrombotic efficacy.

It should be noted that, a blood vessel in which the stent apparatus 1 is to be implanted has sections from which a plurality of rami branch off. If the stent apparatus 1 is implanted at these sections, there is a risk that the stent 2 or the stent covering member 3 will obstruct the entire surface of the inner wall of the blood vessel, thus blocking blood flow to the rami.

In order to solve the above problem, as shown in FIGS. 1 and 3, a plurality of openings 9 are provided in the stent covering member 3 of the present embodiment to ensure blood flow from main blood vessel to rami.

The openings 9 provided in the covering member 3 are formed with 10 to 70% of aperture ratio to the surface area of the blood vessel inner wall covered by the stent 2. In the stent covering member 3, if the aperture ratio of the openings 9 is less than 10%, it will be difficult to ensure blood flow from main blood vessel to rami existing at the region in which the stent 2 is implanted. For this reason, in order to ensure blood flow from main blood vessel to rami, the aperture ratio is required to be 10% or more. On the other hand, if the aperture ratio is more than 70%, sufficient mechanical strength of the covering member 3 is not obtained, so that the stent 2 shape memorized to expanded state cannot be held in contracted state.

Figure 7:
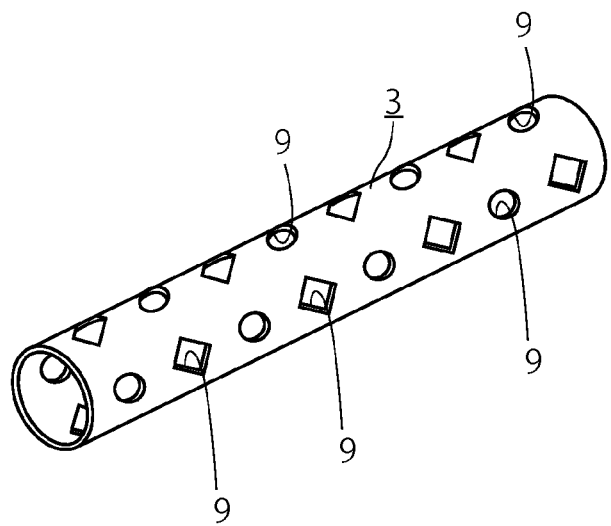
FIG. 7 is a perspective view of another example of a stent covering member constituting a stent apparatus according to the present invention.

It should be noted that the openings 9 provided in the stent covering member 3 can be of any shape including not only circular shape but also triangular and rectangular shapes and, as shown in FIG. 7, different sizes or shapes of openings 9 may be appropriately distributed over the stent covering member 3.

As shown in FIG. 2 explained above, using the stent 2 constituted as a cylindrical body by combining tubular body forming elements 7 formed by bending a continuous strand 4 such that linear parts 5 and bend parts 6 alternate in sequence, and having a sufficient aperture ratio, blood flow to the covering member 3 is promised. In the present invention, therefore, it is preferable to use the stent 2 constituted by combining strands and having large aperture ratio.

In addition, the stent covering member 3 is required to have a certain elasticity to hold the stent 2 in contracted state. As stated above, therefore, the amount of the drug contained in the stent covering member 3 is limited.

Figure 8:
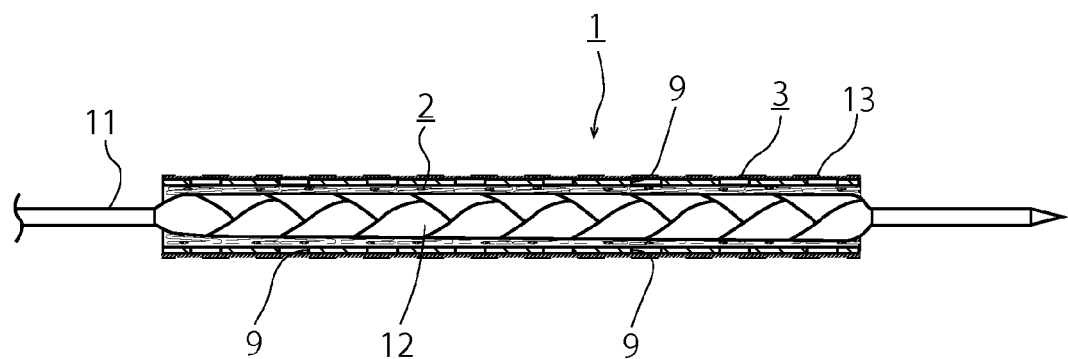
FIG. 8 is a cross sectional view showing a stent covering member containing a drug.

In order to the stent apparatus 1 to contain more amount of drug or various kind of drugs, a drug containing layer 13 may be provided on a surface of the stent covering member 3, as shown in FIG. 8. This drug containing layer 13 may be formed by applying a coating agent, prepared by dissolving one of an anti-platelet agent, an anticoagulant agent and a thrombolytic agent having antithrombotic efficacy and one of an immunosuppressant and an antitumor agent having intimal hyperplasia inhibiting efficacy into a solution in which a copolymer of PLLA and PCL is dissolved into dioxane, to the surface of the stent covering member 3.

Figure 9:
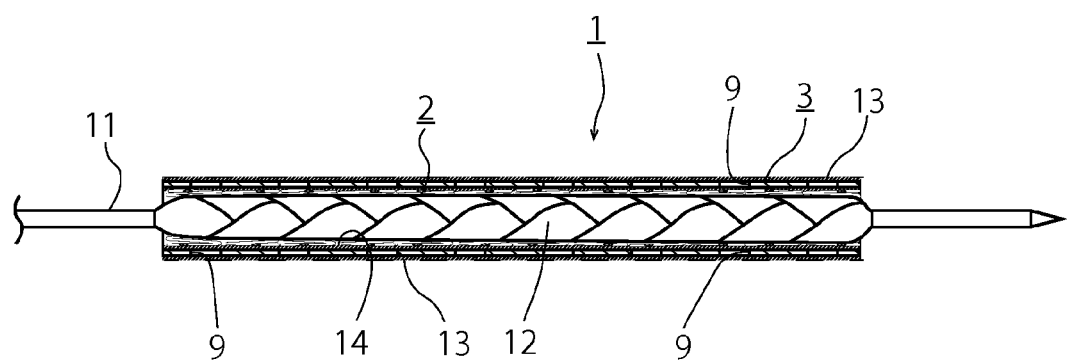
FIG. 9 is a cross sectional view showing another example of a stent covering member containing a drug.

More particularly, after preparing a solution in which a copolymer of PLLA and PCL is dissolved into dioxane, EGCg containing antithrombotic agent in which EGCg is mixed in an antithrombotic agent is dissolved in this solution to form a drug containing solution, and the stent covering member 3 is immersed into this drug containing solution. By taking out this stent covering member 3 from the drug containing solution, as shown in FIG. 9, the drug containing layers 13 and 14 are respectively formed on the outer surface and the lumen which contacts with the outer surface of the stent 2.

In this example, after dissolving 0.5 g of copolymer of PLLA and PCL into 2 ml of dioxiane to produce a solution, 100 mg of EGCg containing antithrombotic agent was dissolved into this solution to prepare a final solution, and then the drug containing layers 13 and 14 were formed by immersing the stent covering member 3 into this final solution and drying it. The stent covering member 3 having an inner diameter of 1 to 3 mm and a length of 10 to 42 mm were used herein to hold the stent 2 in contracted state having a contracted outer diameter of 1 to 3 mm and a length of 10 to 40 mm.

It should be noted that, in the case of forming the drug containing layers on the stent covering member 3 by immersing the stent covering member 3 into a drug containing solution, the stent covering member 3 may be immersed into the drug containing solution in a state in which the stent covering member 3 holds the stent 2. In this case, the drug containing layers are formed on outer and inner surfaces of the stent covering member 3 and a lumen of the stent 2. In addition, the drug containing solution also penetrates into a surface of the stent 2 to form a drug containing layer.

In this way, by forming the drug containing layers 13 and 14 on the inner and outer surfaces of the stent covering member 3, the stent covering member 3 can contain large amount of drug while keeping the elasticity and the other physical properties of the stent covering member 3.

Figure 10:
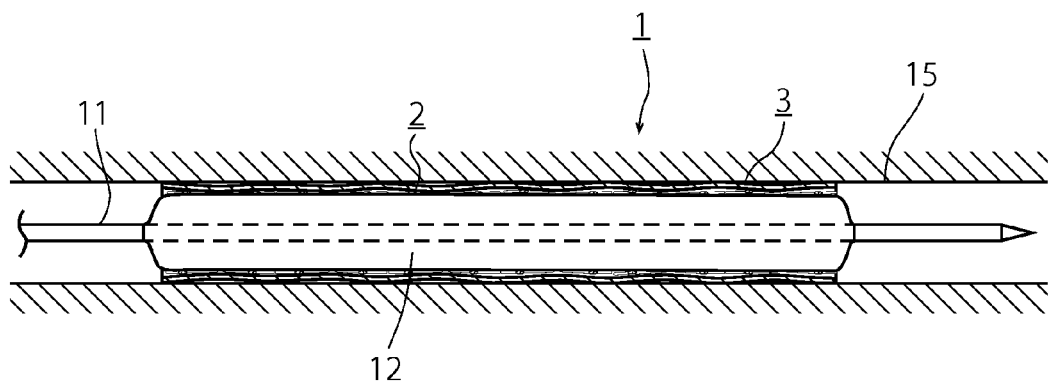
FIG. 10 is a cross sectional view showing a state in which a stent is expanded together with a stent covering member by balloon inflation.
Figure 11:
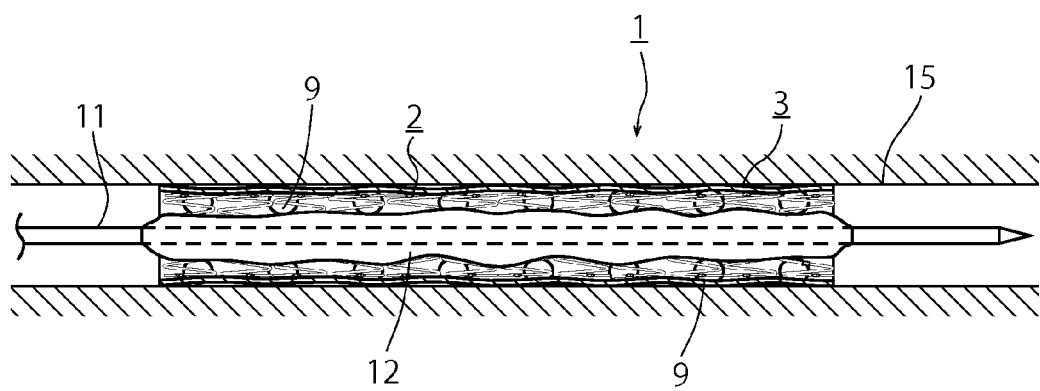
FIG. 11 is a cross sectional view showing a state in which a stent is implanted in a blood vessel.

Next, a process of implanting the stent apparatus 1 constituted as stated above into a lesion site in a blood vessel is now explained. In order to implant the stent apparatus 1 in a blood vessel, as shown in FIG. 6, the stent 2 is mounted on the balloon 12 of the balloon catheter 11 together with the stent covering member 3. At this time, the balloon 12 is in contracted state. The stent apparatus 1 mounted on the balloon 12 is transported together with the balloon catheter through a curved or serpentine blood vessel to a lesion site, which is the implantation site of the stent 2. The stent apparatus 1 transported to the lesion site is expanded in diameter, as shown in FIG. 10, by supplying an expansion media into the balloon 12. When the stent 2 is expanded by inflation of the balloon 12 to a shape memorized size or around it, the stent covering member 3 loses the elasticity and is plastically deformed. When the recovery force to the shape memorized size of the stent 2 exceeds the elastic force of the stent covering member 3, then the stent 2 recovers its shape to the shape memorized expanded size to expand and scaffold the inner wall of the blood vessel 15 by its self-expansion force. Subsequently, the expansion medium supplied to the balloon 12 is drawn to deflate the balloon 12, as shown in FIG. 11, and removing the balloon catheter 11 from the blood vessel 15 completes the implantation process of the stent 2 in the blood vessel.

At this time, the stent covering member 3 unified with the stent 2 is tightly contacts with the inner wall of the blood vessel by pressure of the stent 2 recovering the shape to the shape memorized expanded size, thereby enabling efficient administration of the drug contained therein to the inner wall of the blood vessel.

In this embodiment, since the stent covering member 3 formed of a copolymer of PLLA and PCL has a decomposition rate higher than that of the stent 2 formed of PLLA, it can release the drug in controlled release fashion during the period in which the stent 2 continues to scaffold the blood vessel.

As explained above, employing the present invention provides a stent apparatus wherein a stent shape memorized to expanded state can be implanted in a desired implantation site without dislocation or disengagement against a balloon of a balloon catheter during insertion into a blood vessel, so that the blood vessel can be correctly expanded and scaffolded at this implantation site, while releasing a drug having intimal hyperplasia inhibiting efficacy and/or anti-thrombotic efficacy in controlled release fashion can inhibit intimal hyperplasia and/or thrombosis.

Figure 12:
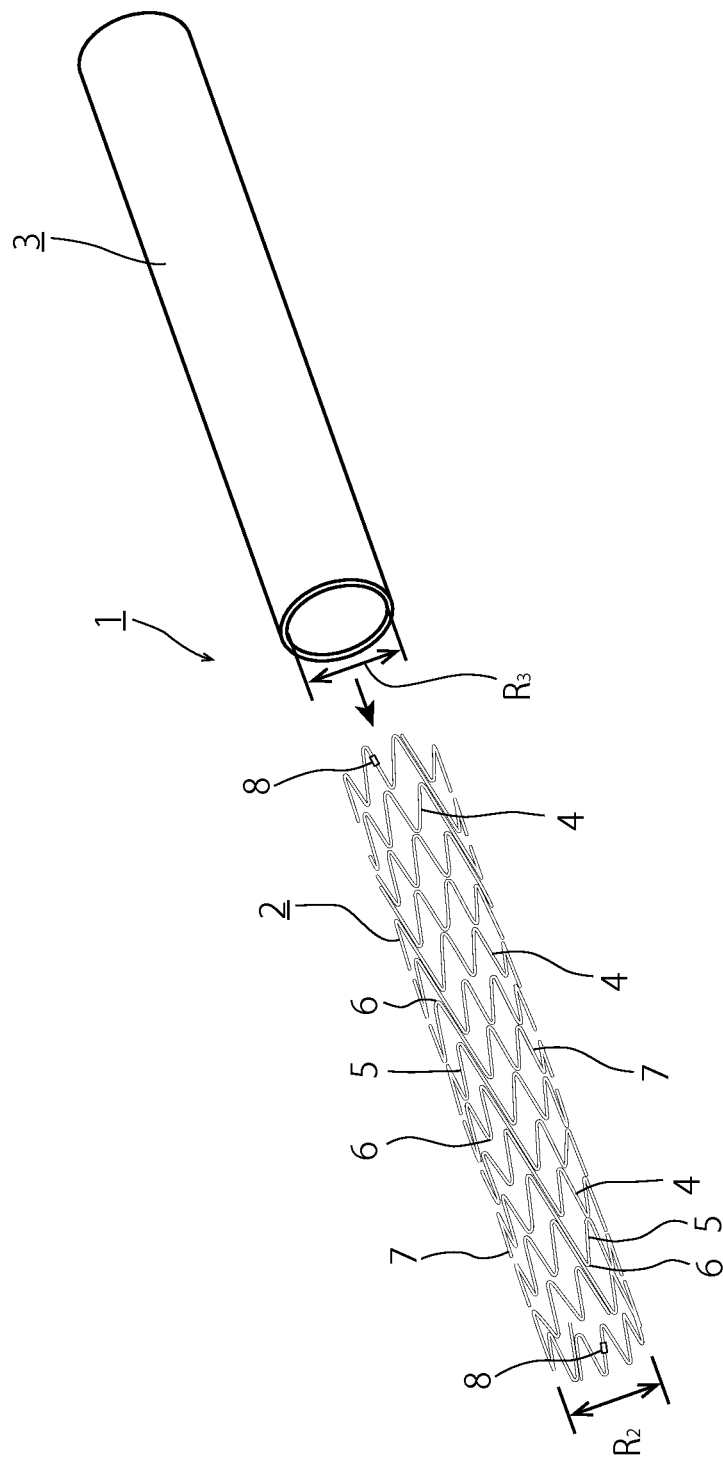
FIG. 12 is a perspective view of another embodiment of a stent apparatus according to the present invention and a stent held by this stent covering member.

It should be noted that, although the above embodiment explains an example in which the stent covering member 3 contains a drug having intimal hyperplasia inhibiting efficacy, the stent covering member 3 may not contain a drug as long as it achieves correct implantation of a stent, which is formed of a biodegradable polymer material, shape memorized to an expanded size larger than an inner diameter of a vessel, and shape recovered by heating of a body temperature when it is inserted into the blood vessel, at a desired implantation site by surely holding the stent in contracted state on a balloon of a catheter. That is, in this invention, the stent covering member 3 may be formed only of a biodegradable material having a certain elasticity and capable of being plastically deformed when it is expanded by a certain amount or more In addition, if the stent apparatus 1 according to the present invention is used at a site not having rami and thus unnecessary to ensure blood flow to rami, the stent covering member 3 may have a flat outer surface without openings as shown in FIG. 12.

It should be noted that the copolymer of PLLA and PLC constituting the stent covering member 3 has a heat shrinkability. The stent covering member 3 may cover the outer surface of the stent 2 by utilizing this heat shrinkability.

Figure 13:
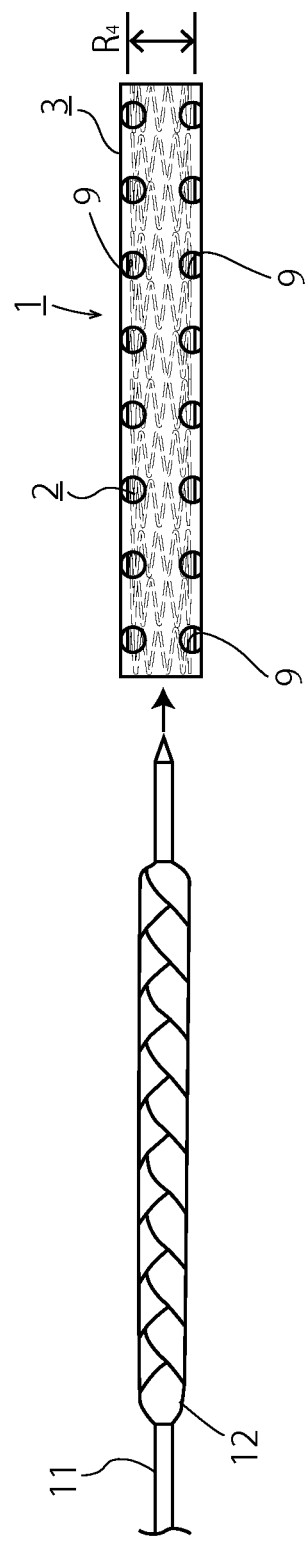
FIG. 13 is a side view showing a state in which a stent covered by a stent covering member is mounted on a balloon of a balloon catheter.

In this case, the stent covering member 3 is formed as a cylindrical shape having an inner diameter R4 slightly larger than the outer diameter R2 of the stent 2 contracted and mounted on a balloon of a balloon catheter. This stent covering member 3 is attached on the contracted stent 2 to cover it. Next, as shown in FIG. 13, the stent 2 covered by the covering member 3 is mounted on the balloon 12 of the balloon catheter 11.

Subsequently, the covering member 3 covering the stent 2 mounted on the balloon 12 is heat treated such that it is heat shrinked to a size having an inner diameter R3 smaller than an outer diameter R2 of the stent 2. By heat shrinking the stent covering member 3 to a cylindrical shape having the inner diameter R3 smaller than the outer diameter R2 of the stent, the stent 2 can be tightly held on the balloon 12.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

REFERENCE SIGNS LIST

1 stent apparatus
2 stent
3 stent covering member
9 opening
11 balloon catheter
12 balloon
13 drug containing layer
14 drug containing layer

What is claimed is:

1. A stent apparatus comprising:
a stent comprising an outer surface and formed of a first biodegradable polymer comprising poly-L-lactide (PLLA), the biodegradable polymer having a shape memory property as a tubular shape and a shape memorized size capable of scaffolding a vessel from an inside of the vessel when implanted in the vessel, wherein the stent is mounted on a balloon of a balloon catheter in a contracted state having a smaller diameter than the shape memorized size before expansion, and
a stent covering member comprising a plurality of openings and an inner surface and for covering the outer surface of the stent contracted and mounted on the balloon of the balloon catheter and expandable by balloon inflation, wherein:
the stent covering member is formed of a second biodegradable copolymer of PLLA and poly-ε-caprolactone (PCL) in which a molar ratio of PLLA to PCL ranges from 95:5 to 20:80,
the first biodegradable polymer and the second biodegradable polymer are configured such that the inner surface of the stent covering member tightly contacts the outer surface of the stent with an affinity to elastically hold the stent in the contracted state,
the stent covering member has elasticity as a cylindrical shape having an inner diameter to keep the stent in the contracted state and, when the stent is expanded to the shape memorized size, plastically deforms to release the stent, wherein the elasticity of the stent covering member decreases during the expansion, the stent covering member formed of the biodegradable copolymer having an elastic force larger than that of the second biodegradable polymer constituting the stent, thereby tightly crimping the outer surface of the stent formed of the first biodegradable polymer and elastically holding the stent in the contracted state, wherein when the expansion exceeds the elastic force of the stent covering member, the stent recovers its shape to the shape memorized size and the stent covering member has an elastic modulus ranging from $2\times10^7$ to $2\times10^9$ Pa at 37 degrees Celsius.

2. The stent apparatus according to claim 1, wherein the stent comprises a tubular body formed by bending a continuous strand to form linear parts and bend parts that alternate in sequence, and the diameter of the stent is expanded and contracted by altering opening angles of the bend parts.

3. The stent apparatus according to claim 1, wherein the plurality of openings have an aperture to surface area ratio of 10 to 70% relative to a surface area of an inner wall of the vessel scaffolded by the stent when the stent is expanded.

4. The stent apparatus according to claim 3, wherein the plurality of openings are configured to ensure blood flow between the inner surface and the outer surface of the stent.

5. The stent apparatus according to claim 1, wherein the stent covering member contains a drug having intimal hyperplasia inhibiting efficacy and the stent contains a drug having antithrombotic efficacy.

6. The stent apparatus according to claim 1, wherein the stent covering member comprises 1 to 30 parts by weight of epigallocatechin gallate (EGCg) with a purity of 94% or more per 100 parts by weight of the biodegradable copolymer.

7. The stent apparatus according to claim 1, wherein a coating agent containing a drug having intimal hyperplasia inhibiting efficacy is applied to an outer surface of the stent covering member to form a drug containing layer.

\* \* \* \* \*